United States Patent [19]

Gibbon

[11] Patent Number: 4,914,717
[45] Date of Patent: Apr. 3, 1990

[54] MICROWAVE ACTUABLE HEATING PAD AND METHOD

[75] Inventor: Robert M. Gibbon, Ft. Worth, Tex.

[73] Assignee: JMK International, Inc., Fort Worth, Tex.

[21] Appl. No.: 309,242

[22] Filed: Feb. 13, 1989

[51] Int. Cl.$^4$ ............................................... H05B 6/80
[52] U.S. Cl. ..................... 219/10.55 M; 219/10.55 F; 128/804; 128/399
[58] Field of Search ................ 219/10.55 M, 10.55 F, 219/10.55 E, 10.55 R, 10.55 D; 128/804, 399, 328

[56] References Cited

U.S. PATENT DOCUMENTS

| | | | |
|---|---|---|---|
| 4,003,840 | 1/1977 | Ishino et al. ................ | 219/10.55 D |
| 4,283,427 | 8/1981 | Winters et al. .............. | 219/10.55 E |
| 4,454,403 | 6/1984 | Teich et al. .................. | 219/10.55 E |
| 4,566,804 | 1/1986 | Collins et al. ........... | 219/10.55 M X |
| 4,602,141 | 2/1986 | Naito et al. .................. | 219/10.55 D |
| 4,743,726 | 5/1988 | Hughes et al. .............. | 219/10.55 F |
| 4,785,148 | 11/1988 | Mayer .......................... | 219/10.55 D |

Primary Examiner—Philip H. Leung
Attorney, Agent, or Firm—Charles D. Gunter, Jr.

[57] ABSTRACT

A device and method are shown for treating a localized area of pain in the human body. A heating pad is applied to the localized area, the pad having a layer of matrix material which is actuable by exposure to microwave energy. The heating pad is heated by exposure to microwave energy to a temperature above ambient prior to application to the localized area. The microwaveable layer is sandwiched between upper and lower elastomeric layers formed from materials which are non-absorptive of microwave energy.

5 Claims, 1 Drawing Sheet

MICROWAVE ACTUABLE HEATING PAD AND METHOD

BACKGROUND OF THE INVENTION

1. Field of the Invention.

The present invention relates generally to therapeutic devices for the treatment of localized injury or pain and specifically, to a microwave actuable heating pad which can be applied to a localized area of the human body for treatment of pain and prevention of injury thereto.

2. Description of the Prior Art.

It is well known that for therapeutic effect, muscle tissue should be heated in some circumstances and chilled in others. For instance, sprained or strained muscle tissues should be chilled to reduce swelling and further damage. Ice packs of various forms are known in the medical art and are commonly applied to localized injury such as sprained or otherwise injured limbs. Small, specialized ice packs are known which are designed for application of cold to localized areas.

Similarly, a variety of devices are known in the prior art for applying heat to localized areas of pain in the human body. Such devices include hot water bottles, which are ordinarily made of flexible rubber, and which can also include insulating coverings for conserving heat when the hot water bottle is filled with hot water. For instance, see U.S. Pat. No. 2,072,564, issued Mar. 2, 1937, to May, entitled "Hot Water Bottle Cover." Other heating devices include electric heating pads in which a plurality of resistive heating elements are electrically actuated to provide a source of heat for treating localized areas of pain.

The prior art hot water bottle suffers from a variety of disadvantages. The device is cumbersome to use, since it is necessary to fill the interior of the bottle with hot water from a tap. Even with an insulating covering, the device lacks the ability to retain a significant amount of heat for a prolonged period of time. The electric heating pad, while more efficient in operation and heat transfer ability suffers from various limitations, such as the encumbrance which results from being attached to a power source by wires. Also, the electric pad can constitute a hazard from electrical voltage if used around water, such as in bath area.

A need exists for an improved device and method for applying heat to localized areas of the human body for the relief of pain and for the prevention and/or treatment of injury.

A need exists for such a device which is heat actuable without the presence of electric wires and which retains its heat transfer properties for a prolonged time period.

SUMMARY OF THE INVENTION

In the method of the invention, a heating pad is applied to a localized area, the heating pad comprising at least one layer of a matrix material having blended therein an electromagnetic absorptive material to produce a homogeneous matrix composition which is heatable by exposure to microwave energy. The homogeneous matrix composition is heated by exposure to microwave energy to a temperature above ambient prior to application to the localized area.

Preferably, the matrix material is provided by blending a silicone rubber composition with an electromagnetic absorptive material to produce a homogeneous matrix composition which is heatable by exposure to microwave energy in a microwave oven. The homogeneous matrix composition can be blended from a polyorganosiloxane gum, a particulate electromagnetic absorptive material, a filler and a curing catalyst to produce a homogeneous matrix composition which is heatable by exposure to microwave energy. The layer of microwaveable silicone rubber is preferably sandwiched between an upper and lower elastomeric layers formed from materials which are non-absorptive of microwave energy. For instance, the upper and lower layers can be formed of an organic rubber having a low thermal conductivity rating. The sandwiched microwaveable silicone rubber can also be covered with a cloth pouch, if desired.

Additional objects, features and advantages will be apparent in the written description which follows.

DETAILED DESCRIPTION OF THE INVENTION

Figure 1:
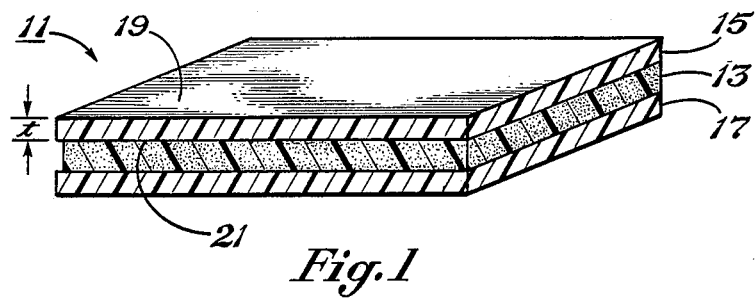
FIG. 1 is a perspective view, partially in section, of a heat pad of the invention showing a microwaveable which is sandwiched between upper and lo non-absorptive materials.

Turning to FIG. 1, there is shown a heating pad of the invention designated generally as 11. The heating pad 11 comprises at least one layer 13 of a matrix material having blended therein an electromagnetic absorptive material to produce a homogeneous matrix composition which is heatable by exposure to microwave energy. The matrix material can comprise any of a number of commercially available flexible, elastomeric materials. For instance, the matrix material can be, e.g., natural rubber, synthetic rubber, styrene butadiene rubber, ethylene propylene rubber, cloroprene, nitrile rubber and silicone rubber. The criteria for selecting a candidate material are its flexibility after curing to allow application to the affected area of the body, its heat stability, and the ability to be heat actuated by exposure to electromagnetic energy. The preferred material is silicone rubber because of its heat stability and its superior resistance to embrittlement due to oxidation, ozone attack and general use.

The preferred matrix material for the microwaveable layer 13 can be manufactured by blending together a polyorganosiloxane gum with a particulate electromagnetic absorptive material to produce a homogeneous, silicone rubber composition which is heatable by exposure microwave energy. The organopolysiloxane polymers or gums employed in the preferred matrices of the invention are well known materials and can be made by standard methods known in the art. The preferred polymer is an organopolysiloxane gum which contains methyl, vinyl, phenyl and/or 3, 3, 3-trifluropropyl radicals attached to the silicone atoms of the polymeric siloxane. Examples of organopolysiloxane gums are those polymers, copolymers and mixtures thereof wherein the siloxy units can be dimethylsiloxane, phenylmethylsiloxane, 3, 3, 3-trifluoropropylmethyl siloxane, diphenylsiloxane, methylvinylsiloxane, and phenylvinylsiloxane. A discussion of the preparation of such compounds can be found, for example, in: Eaborn, D., "Organo Silicone Compounds", Academic Press, New York, 1959; Montermoso J. C., "Silicone Rubbers", Morton, E. D., "Introduction to Rubber Technology", Reinhold Publishing Corp., New York, 1959; Rochow, E.G., "An Introduction to the Chemistry of Silicones", to Ed. John Wiley and Sons, New York, 1951.

The organopolysiloxane polymer used in the method of the invention is most preferably a dimethyvinylsiloxyended polydiorganosiloxane having a percentage of all organic radicals in the gum, 99.80 percent by weight methyl radicals and about 0.2 percent by weight vinyl radicals. A preferred polymer has a specific gravity in the range from about 1.24–1.29 and a durometer of about 40–55.

In order to provide a matrix composition which is microwave heatable, a particulate, electromagnetic absorptive material is blended with the matrix material. A number of such materials are commercially available, including ferrites, powdered iron, powdered aluminum, and zinc oxide. The preferred absorptive material is zinc oxide and when blended in the range from about 5 to 30 parts per 100 parts polyorganosiloxane gum produces a silicone rubber blend which is heatable in the range of 160°–180° F. by exposure to a 700 watt microwave oven for 1 to 5 minutes. The matrix composition should require on the order of 40–50 minutes to return to 60° F.

The polyorganosiloxane gum can contain any of the conventional filler materials. These filler materials are well known in the art and are commercially available from a number of sources. The preferred material is a silica filler, sometimes referred to an reinforcing filler, or a mixture of silica filler and an extending filler. Examples of silica filler which can be utilized to reinforce the organopolysiloxane elastomer are fumed silica, precipitated silica, silica aerogel, etc. The filler material, including reinforcing and non-reinforcing fillers, is preferably used in the range of about 10–260 parts of filler per 100 parts of organopolyorganosiloxane gum or elastomer, most preferably in the range of about 20 to 80 parts of filler.

Various curing agents can be employed to effect the more rapid conversion of the polyorganosiloxane compositions to the cured, solid elastic state. For example, benzoyl peroxide, bis (2,4-dichlorobenzoyl) peroxide, and the like. These curing agents are normally present in the polyorganosiloxane composition in an amount ranging from about 0.1 to high as 4 to 8 parts or more based on 100 parts of organpolysiloxane blend.

In addition to the above described ingredients, the silicone rubber matrix compositions of the invention can contain heat stability additives, compression set additives, additives to improve handling properties, dyes or coloring additives and other additives conventionally used in heat cured silicone elastomers and also room temperature cure elastomers.

The preferred microwaveable silicone rubber matrix composition is made by blending or milling together the various constituents. The order of adding the elastomer, filler, curing agent, and electromagnetic absorptive material is not critical. The following example is intended to be illustrative of the invention:

Polyorganosiloxane Gum: 60.0
Zinc Oxide*: 15.0
Fume Silica: 23.0
Structure Control Fluid: 2.0
Pigment (Blue): 0.6
Benzoyl Peroxide Catalyst: 0.6
*Nodular, pure grade zinc oxide having a high surface area (7 sq.m/gm.).

As shown in FIG. 1, the microwave actuable layer 13 is preferably sandwiched between upper and lower insulating layers 15, 17. The layers 15, 17 are planar members, each of which has a top planar surface 19 a bottom planar surface 21 separated by a thickness "t."  Layers 15 and 17 are formed from flexible materials which are non-absorptive of microwave energy. For example, upper and lower layers 15, 17 can be formed of an organic rubber having a low thermal conductivity rating, or can be formed of a low gravity silicone rubber having a relatively high silicone content and a relatively low extending filler content and omitting the electromagnetic absorptive material. For instance, composition could comprise about 60–70% polyorganosiloxane gum and about 15–20% filler as contrasted to the microwaveable matrix composition. In general, the lower the thermal conductivity of layers 15 and 17, the better the insulating properties. These layers can, therefore, be an organic rubber which is not carbon-reinforced or one which in not receptive to microwave energy. The upper and lower layers 15, 17 are preferably bonded to the mid-layer 13, as by bringing the partially cured layers into contact and then final curing, or through the use of a suitable adhesive. For example, an RTV silicone adhesive could be utilized.

It should also be noted that the relative thickness of the layers 13, 15 and 17 determines, to some extent, the heat loss characteristics of the blanket. As the mid-layer 13 increases in thickness, the longer the blanket must be exposed to microwave energy to increase its temperature. The pad will then take longer to cool, however, because of the extra heat in the mid-layer 13. The thickness of the upper and lower layers 15, 17 determines the characteristic cooling cycle for the pad. The thicker the layer, the longer the cool down time for the pad. Preferably the mid-layer 13 has a thickness in the range from about ¼" to ¾" and the upper and lower layers have a thickness in the range from about ¼" to ¾".

Figure 2:
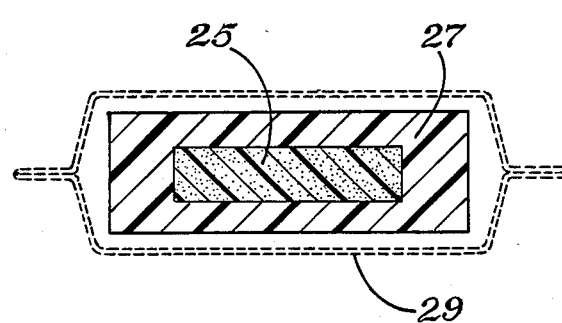
FIG. 2 is a side, cross-sectional view of a heating pad of the invention showing a centrally located microwaveable layer which is encapsulated with non-absorptive material, the non-absorptive material being covered with a cloth pouch which is shown in dotted lines.

As shown in FIG. 2, the heating pad can be provided as a layer of microwaveable silicone rubber 25 which is completely encapsulated within an outer elastomeric body 27. The outer elastomeric body can, in turn, be covered with a cloth pouch 29 which can be calendared onto the surface of the elastomeric body 27 or stitched in the form of an envelope. Preferably, the cloth is heat resistant in the preferred temperature operating ranges of the invention.

Figure 3:
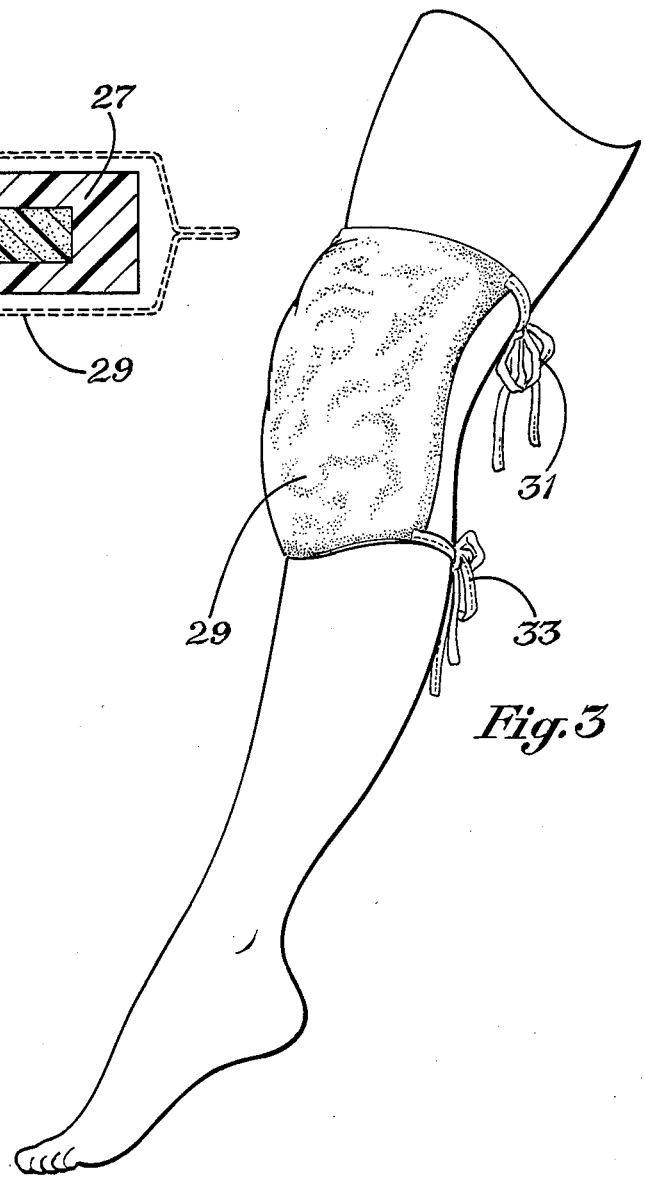
FIG. 3 is a side, elevational view of a cloth covered heating pad of the invention wrapped about the knee joint of and attached by tie straps.

The primary use for the heating pad of the invention would be as a therapeutic device for relieving localized pain, such as back pain. Any localized area can be treated, however, such as the knee joint. As shown in FIG. 3, the pad 11 can conveniently be provided with a cloth pouch and attaching ties 31, 33 which allow the pad to be carried on the knee of a wearer. In use, the pad 11 is first heated in a microwave oven to the appropriate operating temperature. For instance, using a 700 watt microwave oven at 100% power for 3 minutes, a ⅜" thick pad having three plys, each ply being ⅛" thick reaches a preferred operating temperature of approximately 170°F. It then takes the pad approximately 45 minutes to return to 60°F.

An invention has been provided with several advantages. The heating pad of the invention can be used for a variety of medical applications without the encumbrance of being attached to a power source by wires. Also, the pad of the invention does not represent a hazard from the electric source, even if water is present. The pad can be easily attached to an affected location, such as the limb of the wearer while allowing movement of the limb. The pad is simple and economical to manufacture and is not easily damaged in use.

While the invention has been shown in only one of its forms, it is not thus limited but is susceptible to various changes and modifications without departing from the spirit thereof.

I claim:

1. A method of treating a localized area of pain in the human body, comprising the steps of:

applying a heating pad to the localized area, the heating pad comprising at least one layer of microwaveable silicone rubber which has been heated by exposure to microwave energy to a temperature above ambient prior to application to the localized area the microwaveable silicone rubber comprising a polyorganosiloxane gum having blended therein about 5 to 30 parts per 100 parts of gum of zinc oxide as an electromagnetic absorptive material and from about 10 to 260 parts per 100 parts of gum of a filler material; and wherein said one layer of microwaveable silicone rubber is sandwiched between an upper and a lower elastomeric layers formed from materials which are non-absorptive of microwave energy, said upper and lower elastomeric layers having a lower relative extending filler content than said microwaveable silicone rubber layer, whereby said heating pad is heatable to approximately 170°F. by exposure to a 700 watt microwave oven at 100% power for 3 minutes, the pad requiring approximately 45 minutes to return to 60°F.

2. The method of claim 1, wherein said upper and lower layers are formed of an organic rubber having a low thermal conductivity rating.

3. The method of claim 1, wherein said upper and lower layers are formed of a low gravity silicone rubber having a relatively high silicone content and a relatively low extending filler content.

4. The method of claim 1, wherein said upper and lower elastomeric layers completely encapsulate said one layer of microwaveable silicone rubber.

5. The method of claim 4, wherein said upper and lower elastomeric layers are covered with a cloth pouch.

* * * * *